(12) United States Patent
Monahan et al.

(10) Patent No.: US 10,761,029 B1
(45) Date of Patent: Sep. 1, 2020

(54) LASER-INDUCED SPECTROSCOPY SYSTEM AND PROCESS

(71) Applicant: Schenck Process LLC, Kansas City, MO (US)

(72) Inventors: Randy James Monahan, Strongsville, OH (US); John Joseph Nowakowski, Richfield, OH (US); Lauren Elizabeth Callahan, Medina, OH (US); Geoffrey K. Urbanek, Streetsboro, OH (US)

(73) Assignee: Schenck Process LLC, Kansas City, MO (US)

( * ) Notice: Subject to any disclaimer, the term of this patent is extended or adjusted under 35 U.S.C. 154(b) by 0 days.

(21) Appl. No.: 16/561,638

(22) Filed: Sep. 5, 2019

(51) Int. Cl.
*G01J 3/30* (2006.01)
*G01N 21/71* (2006.01)
*G01N 33/22* (2006.01)
*G01N 21/01* (2006.01)

(52) U.S. Cl.
CPC .......... *G01N 21/718* (2013.01); *G01N 21/01* (2013.01); *G01N 33/222* (2013.01)

(58) Field of Classification Search
CPC ............... G01N 21/718; G01N 21/645; G01N 21/6458; G01J 3/4406; G01J 3/02
USPC .......................................................... 356/318
See application file for complete search history.

(56) References Cited

U.S. PATENT DOCUMENTS

| | | | |
|---|---|---|---|
| 6,771,368 B1 | 8/2004 | Chadwick | |
| 8,619,255 B2 | 12/2013 | Gennadievich | |
| 2014/0227458 A1* | 8/2014 | Karakawa | H01J 37/32972 427/569 |
| 2015/0138545 A1* | 5/2015 | Day | G01N 21/718 356/318 |
| 2016/0084709 A1* | 3/2016 | Day | G01J 3/30 356/318 |

* cited by examiner

*Primary Examiner* — Md M Rahman
(74) *Attorney, Agent, or Firm* — Hovey Williams LLP

(57) ABSTRACT

Specialized linkage assemblies for Laser-Induced Breakdown Spectroscopy ("LIBS") systems are provided. The linkage assemblies may facilitate the attachment of the laser housing of the LIBS system onto an existing sample supply chamber, such as a volumetric or gravimetric feeder. Generally, the linkage assemblies may comprise a specialized purge head and inert gas assembly that facilitate the attachment of the laser housing and may enhance the functionality of the LIBS system.

20 Claims, 5 Drawing Sheets

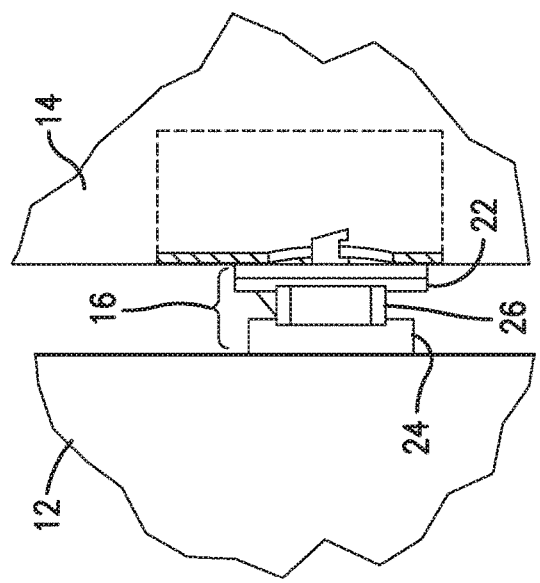
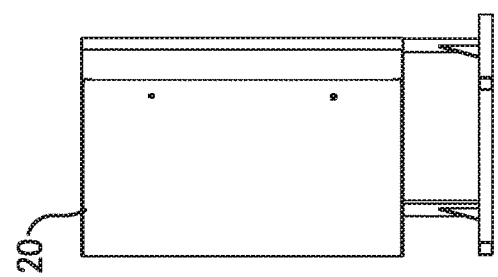
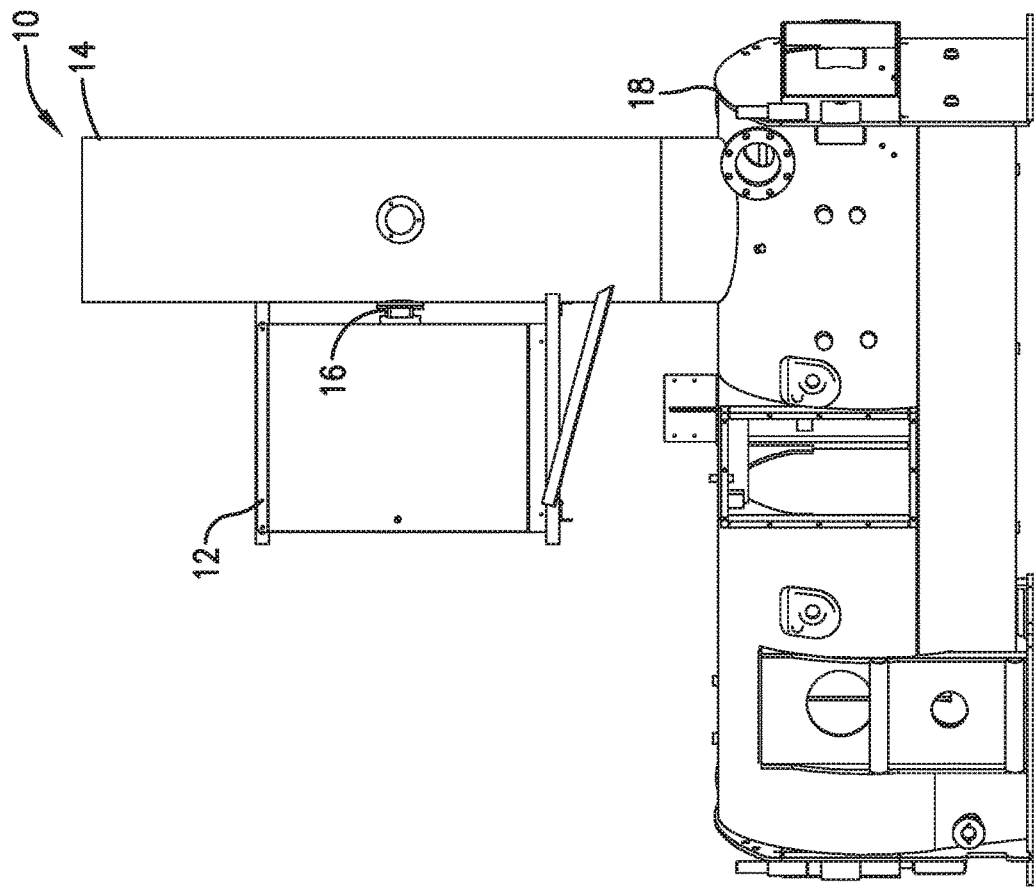

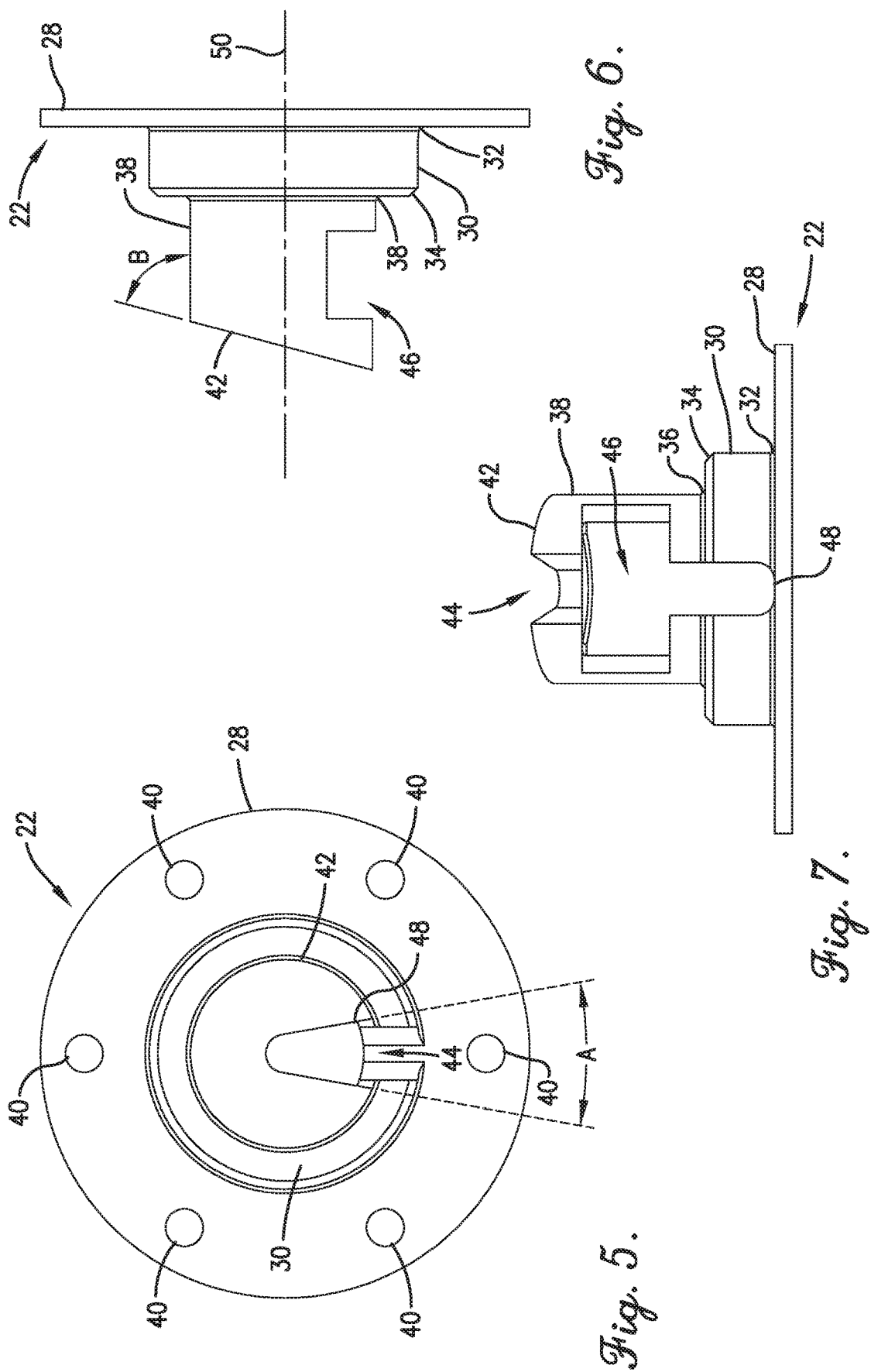

US 10,761,029 B1

LASER-INDUCED SPECTROSCOPY SYSTEM AND PROCESS

BACKGROUND

1. Field of the Invention

The present invention generally relates to Laser-Induced Breakdown Spectroscopy ("LIBS") systems. More particularly, the present invention generally relates to linkage assemblies that may be used in LIBS systems.

2. Description of the Related Art

Laser-Induced Breakdown Spectroscopy ("LIBS") is a technique that uses pulsed laser energy to breakdown a small amount of material. More particularly, the laser is used to ionize the material and form localized plasma, which is a continuum of light frequencies radiated from the material. These light frequencies are collected and analyzed to determine the chemical makeup of the ablated material. With this data, one can easily output a variety of information specific to a sample material, such as moisture content, ash content, calorific value, and ash fusion temperature.

Despite the use and advancements of LIBS technology, it may be difficult to incorporate a LIBS system into existing feeding systems. Thus, there is still a need for new and efficient systems and methods for linking a LIBS system to existing systems and structures.

SUMMARY

One or more embodiments of the present invention generally concern a linkage assembly for a laser-induced breakdown spectroscopy system. Generally, the linkage assembly comprises a purge head comprising: (a) a base for connecting the purge head to the linkage assembly; (b) a protrusion protruding from the base for at least partially extending into a sample supply chamber, the protrusion comprising a tapered front face and a slot opening positioned between the base and the front face; and (c) a perforation extending through the base and the protrusion, wherein the perforation is configured to allow a laser to pass through and contact a sample.

One or more embodiments of the present invention generally concern a laser-induced breakdown spectroscopy system. Generally, the laser-induced breakdown spectroscopy system comprises: (a) a laser housing comprising a laser source and a spectrometer and (b) a linkage assembly for connecting the laser housing to a sample supply chamber. Furthermore, the linkage assembly comprises a purge head that contains: (i) a base for connecting the purge head to the linkage assembly; (ii) a protrusion protruding from the base for at least partially extending into a sample supply chamber, the protrusion comprising a tapered front face and a slot opening positioned between the base and the front face; and (iii) a perforation extending through the base and the protrusion, wherein the perforation is configured to allow a laser to pass through and contact a sample.

One or more embodiments of the present invention generally concern a method for operating a laser-induced breakdown spectroscopy system. Generally, the method comprises: (a) providing a laser housing comprising a laser source and a spectrometer connected to a sample supply chamber via a linkage assembly and (b) contacting the sample with the laser when at least a portion of the sample contacts the tapered front face of the purge head. Furthermore, the linkage assembly comprises a purge head that contains: (i) a base for connecting the purge head to the linkage assembly; (ii) a protrusion protruding from the base for at least partially extending into a sample supply chamber, the protrusion comprising a tapered front face and a slot opening positioned between the base and the front face; and (iii) a perforation extending through the base and the protrusion, wherein the perforation is configured to allow a laser to pass through and contact a sample.

BRIEF DESCRIPTION OF THE FIGURES

Embodiments of the present invention are described herein with reference to the following drawing figures, wherein:

FIG. 1 depicts an exemplary embodiment wherein a LIBS system is incorporated within a coal feeding system;

FIG. 2 depicts an enlarged depiction of the linkage assembly from FIG. 1;

FIG. 5 depicts a front elevation view of the purge head of the linkage assembly according to one embodiment of the present invention;

FIG. 6 depicts a side elevation view of the purge head of the linkage assembly according to one embodiment of the present invention;

FIG. 7 depicts a bottom plan view of the purge head of the linkage assembly according to one embodiment of the present invention;

DETAILED DESCRIPTION

Figure 4:
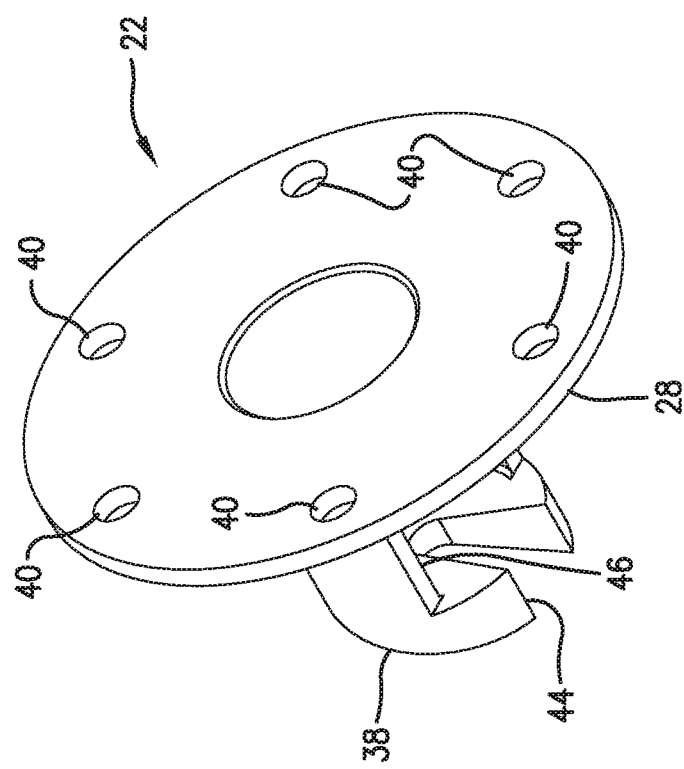
FIG. 4 depicts a back perspective of the purge head of the linkage assembly according to one embodiment of the present invention.

LIBS systems allow for a real-time analysis of various types of particulate-based materials present in existing feeding systems. More particularly, the LIBS systems can be mounted onto a sample supply chamber, such as a sample feeder downspout, so that the LIBS system can instantly analyze the particulate-based feed stream in real-time while the feed stream is being introduced into a plant or reactor. However, there can be performance and durability issues when incorporating a LIBS system into an existing feeding system that utilizes a particulate-based feed stream.

The linkage assemblies of the present invention are able to address many of the previous deficiencies associated with incorporating a LIBS system into an existing feeding system. More particularly, the linkage assemblies of the present invention may be used to facilitate the attachment of a LIBS system onto an existing feeding system and enhance the functionality and operation of the LIBS system. As described below in greater detail, the linkage assemblies of the present invention may utilize a specialized purge head and/or a specialized inert gas assembly to provide the desired functionality of the linkage assemblies described herein.

FIG. 1 depicts an exemplary LIBS system 10 comprising a linkage assembly 16 that may be employed in conjunction with a coal feeding system 18. It should be understood that the LIBS system shown in FIG. 1 is just one example of a system within which the present invention can be embodied. Thus, the present invention may find application with a wide variety of other particulate-based feeding systems where it is desirable to efficiently and effectively analyze a particulate-based feed stream during operation. The exemplary LIBS system 10 illustrated in FIG. 1 will now be described in greater detail.

As shown in FIG. 1, the primary components of the LIBS system 10 include a laser cabinet 12, a linkage assembly 16, a control cabinet 20, and an inert gas source (not depicted in FIG. 1). Generally, the laser cabinet 12 may contain a 100 MJ laser, focusing optics, return optics, spectrometer, and mirrors. The laser cabinet 12, along with the linkage assembly 16, may be mounted directly to a sample supply chamber 14, such as the coal feeder downspout 14 depicted in FIG. 1. As demonstrated in FIG. 1, the linkage assembly 16 connects the laser cabinet 12 with the sample supply chamber 14. Moreover, as shown in FIG. 1, the coal feeder downspout 14 can directly flow into an existing feeding system 18, which can feed a particulate feed stream, such as coal, into a plant or reactor.

The control cabinet 20 comprises the hardware for controlling the laser and other components in the laser cabinet 12 and may include, for example, a computer, a pulse delay generator, a laser control, a cooling system, and data analysis tools. The control cabinet 20 may sit on the floor and communicate with the laser cabinet 12.

Conventional LIBS systems, including the laser configurations and setups, are described in U.S. Pat. Nos. 6,771,368 and 8,619,255, the disclosures of which are incorporated herein by reference in their entireties.

Knowing the chemical makeup of a particulate feed stream, such as coal, in real time can allow one to better control the operation of a plant or reactor. The LIBS system 10 in FIG. 1 allows the analytical measurement of a particulate feed stream, such as coal, before the time of feeding, which can facilitate the diagnosis and control of a coal stack output. More particularly, the LIBS system 10 may allow the feeding of a particulate feedstock, such as coal, at a constant energy rate by measuring and evaluating various characteristics of the incoming particulate feedstock in real-time before it is introduced into the actual feeder. For example, the LIBS system 10 may measure the chemical composition, total ash content, and/or ash species concentrations of a particulate feedstock prior to its introduction into a feeding system.

The sample supply chamber 14 in FIG. 1 is depicted as a gravimetric-based downspout; however, it is envisioned that the LIBS system 10 and linkage assembly 16 of the present invention may be used with a variety of sample supply chambers including, for example, other types of gravimetric-based feeders and/or volumetric-based feeders that function with other types of particulate-based samples.

The linkage assembly 16 for connecting the laser cabinet 12 to the sample supply chamber 14 is more closely depicted in FIG. 2. As shown in FIG. 2, the linkage assembly 12 may comprise a purge head 22, an inert gas assembly 24, and a zero-leak valve 26. The zero-leak valve 26 can include any valve known in the art that may prevent fluid flow between the purge head 22 and the inert gas assembly 24. In certain embodiments, the zero-leak valve may comprise a slide gate valve.

The purge head 22 can be used to directly connect the linkage assembly 16 and laser cabinet 12 to the sample supply chamber 14. As shown in FIG. 2, the base of the purge head 22 may be attached to the sample supply chamber 14, while a protrusion from the purge head 22 extends into the sample supply chamber 14 to collect particulate samples therein.

As depicted in FIG. 2, the purge head 22 is designed so that at least a portion of the purge head 22 can be placed into the flow of moving particulate material within the sample supply chamber 14. This configuration allows for the particulate sample material to pass across the front face of the purge head 22 and expose the sample material to the laser coming from the laser cabinet 12.

Figure 3:
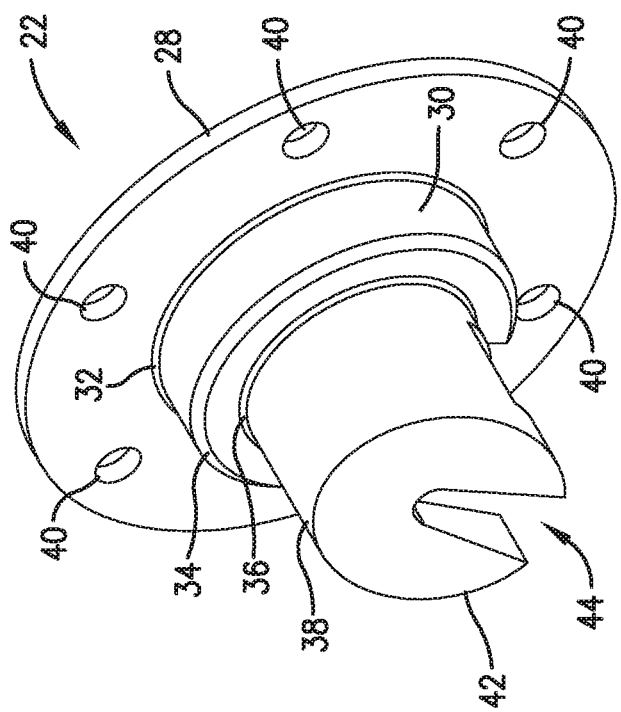
FIG. 3 depicts a front perspective of the purge head of the linkage assembly according to one embodiment of the present invention.

FIGS. 3-7 provide various depictions of the purge head 22. As shown in FIGS. 3, 6, and 7, the purge head 22 may comprise an overall base comprising a mounting base 28, an extended base 30, a first chamfer 32, a second chamfer 34, and a third chamfer 36. The base is designed to support a protrusion 38 of the purge head 22 that extends from the base into the sample supply chamber. As shown in FIG. 2, the base can attach the purge head 22 to the linkage assembly and sample supply chamber via the mounting base 28. The mounting base 28 may comprise a plurality of attachment apertures 40, wherein a bolt or other connection means can be introduced.

The protrusion 38 of the purge head 22 facilitates the flow of the particulate sample material across the laser sight at a predetermined distance within the sample supply chamber. Consequently, this can create a uniform flow of the particulate sample across the laser's detection position within the sample supply chamber. Thus, the purge head 22 is important because it allows the LIBS system to get access to the sample material inside the moving sample supply chamber and it provides consistent location of the sample material within the sample supply chamber relative to the laser focus point. In various embodiments, the purge head 22 may comprise a ratio of the length of the protrusion 38 to the length of the base (including 28, 30, 32, 34, and 36) of at least 1:1, 1.5:1, 1.8:1, or 2:1 and/or less than 10:1, 9:1, 8:1, 7:1, 6:1, 5:1, or 4:1. It should be noted that all "length" measurements are measured along the direction of the longitudinal axis 50 of the purge head 22.

As shown in FIGS. 3, 5, and 6, the protrusion 38 may comprise a tapered front face 42. This tapered front face 42 of the protrusion 38 may cause the particulate sample material in the sample supply chamber to contact the face surface of the purge head 22 during operation of the LIBS system. As shown in FIG. 6, the tapered front face 42 of the purge head 22 may have an angle (B) of at least 25, 30, 35, 40, 45, 50, 55, 60, 65, or 70 degrees and/or less than 90, 85, or 80 degrees relative to the longitudinal axis 50 of the purge head.

Additionally, as shown in FIGS. 3-5 and 7, the protrusion 38 may comprise a shaped opening 44 present on the front face of the purge head 22. As shown in FIGS. 4 and 7, this shaped opening 44 may extend longitudinally from the tapered front face 42 of the purge head 22 into the slot opening 46 and laser perforation 48. The shaped opening 44 on the tapered front face 42 may function as the primary contact area for the laser to contact the particulate sample material as it contacts the tapered front face 42 of the purge head 22. The defined shape of the shaped opening 44 can be specific to prevent the particulate sample material from getting stuck and accumulating within the purge head 22. As shown in FIG. 5, the diameter of the shaped opening expands from a position extending downward from a longitudinal axis 50 of the purge head 22 to the opening at the bottom surface of the tapered front face 42. In various embodiments, the shaped opening 44 may comprise a U-shaped or V-shaped opening. As shown in FIG. 5, in one or more embodiments, the shaped opening may comprise an angle (A) of at least 5, 10, 15, or 20 degrees and/or less than 90, 80, 70, 60, 50, 40, 35, 30, or 25 degrees.

Due to their unique shapes, the tapered front face 42 and the shaped opening 44 may achieve the desired effect of setting the sample particulate material in the same position relative to the laser focusing optics. Moreover, the tapered front face 42 and the shaped opening 44 may also facilitate the self-cleaning of the laser target area within the sample supply chamber as the shapes of these components may help prevent the buildup of the sample material at the laser target area.

As shown in FIGS. 4, 6, and 7, the protrusion 38 may comprise a slot opening 46 on the bottom side of the protrusion 38. During laser firing and the ablation of sample material, a minor explosion of the sample may occur, and small pieces of sample material may be ejected into the body of the purge head 22. However, this exploded material may be allowed to escape from the purge head 22 through the slot opening 46 in the bottom of the purge head 22 due to gravity. Without the slot opening 46, the exploded sample material could agglomerate inside the purge head 22 and eventually block the laser beam path. Generally, the total volume of the slot opening 46 can be greater than the total volume of the shaped opening 44. In various embodiments, the purge head 22 comprises a ratio of the overall body length of the purge head to the length of slot opening of at least 1.5:1, 2:1, 2.5:1, or 3:1 and/or less than 10:1, 9:1, 8:1, 7:1, 6:1, 5:1, or 4:1.

Furthermore, as depicted in FIG. 7, the purge head 22 may comprise a perforation 48 extending through the base of the purge head 22 and the protrusion 38. This perforation 48 may be configured to allow a laser to pass through the purge head 22 and contact a sample in the sample supply chamber. In various embodiments, as shown in FIG. 7, the shaped opening 44 comprises a maximum width at the bottom of the shaped opening 44. In such embodiments, the maximum width of the shaped opening 44 can be greater than the average width of the perforation 48. In one or more embodiments, the purge head 22 may comprise a ratio of the average width of the perforation 48 to the maximum width of the shaped opening 44 of at least 1.5:1, 2:1, 2.5:1, or 3:1 and/or less than 10:1, 9:1, 8:1, 7:1, 6:1, 5:1, or 4:1. In one or more embodiments, the protrusion 38 constitutes at least 25, 30, 35, 40, 45, 50, 55, 60, or 65 percent of the overall length of the purge head 22.

Generally, the purge head may be designed and manufactured out of various metal alloys, preferably stainless steel. Moreover, in various embodiments, the purge head 22 may be coated with a spray-on durability coating to help increase the durability of the purge head 22. Exemplary durability coatings may include ceramic-based coatings.

Turning now to the inert gas assembly 24, various views of the inert gas assembly 24 are provided in FIGS. 8-12. As shown in FIGS. 8-12, the inert gas assembly 24 may comprise an inert gas flange 54 and a removable lens housing 56 placed within an aperture of the inert gas flange 54. In addition, the inert gas flange 54 may comprise multiple connection apertures 58 to facilitate the introduction of bolts so that the inert gas assembly 24 may be attached to the purge head 22 and zero-leak valve 26. Furthermore, the inert gas flange 54 may also comprise other connection apertures 60 to facilitate the introduction of bolts so that the inert gas assembly 24 may be attached to the laser cabinet 12.

Figure 10:
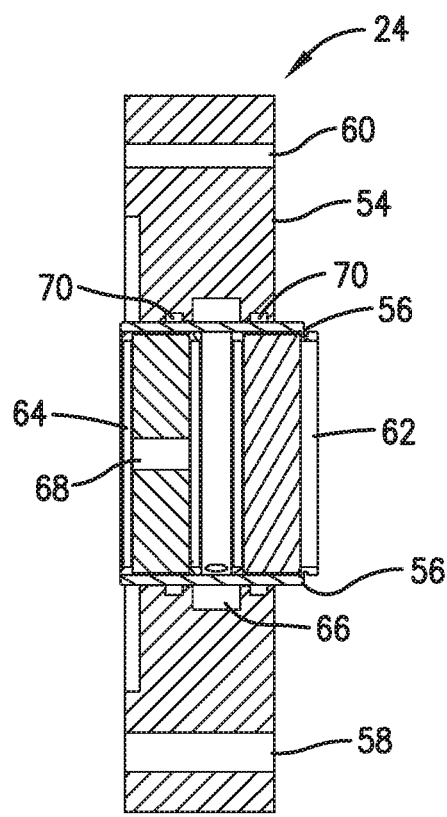
FIG. 10 depicts a side elevation view of the inert gas assembly of the linkage assembly according to one embodiment of the present invention.
Figure 11:
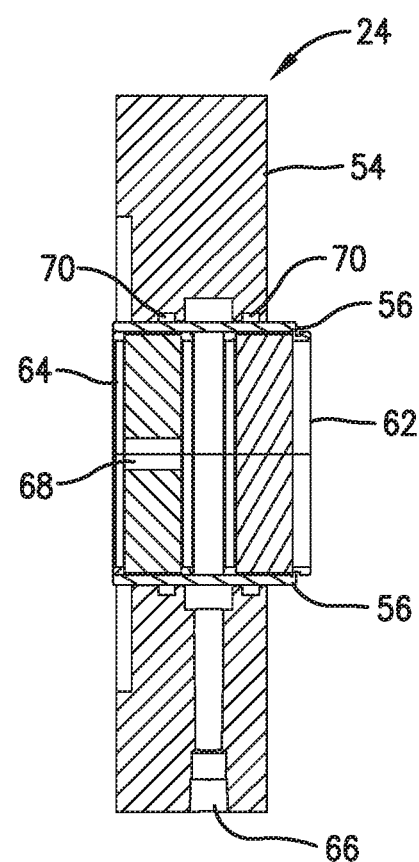
FIG. 11 depicts a side elevation view of the inert gas assembly of the linkage assembly according to one embodiment of the present invention.
Figure 12:
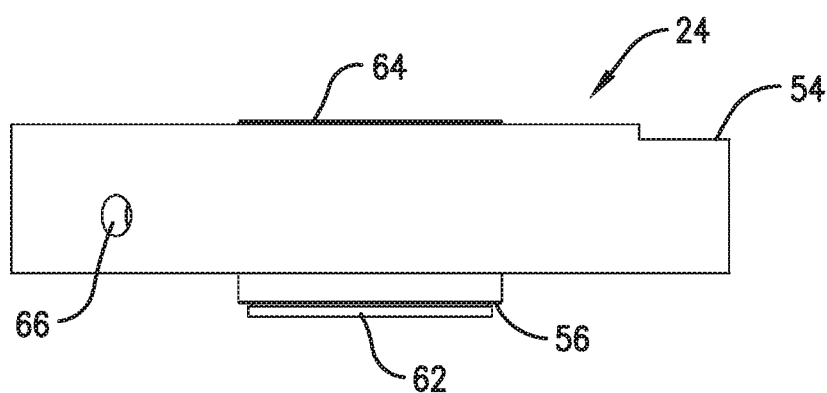
FIG. 12 depicts a side perspective of the inert gas assembly of the linkage assembly according to one embodiment of the present invention.

As shown in FIGS. 10-12, the inert gas flange 54 may comprise an inert gas intake 66 configured to transfer and introduce an inert gas into the inert gas flange 54 and the lens housing 56. The inert gas intake 66 can be in the form of tubing, boreholes, or piping configured to transfer an inert gas from an inert gas source. In certain embodiments, the inert gas can comprise argon gas.

Due to the configuration depicted in FIGS. 8-12, the resulting inert gas assembly 24 can form a gas-tight assembly that forces the inert gas, such as an argon gas, through the zero-leak valve 26 and the perforation of the purge head 22 and into the sample supply chamber 14. The inert gas may provide numerous benefits to the linkage assembly 16 and the LIBS system 10. For example, the inert gas assembly 24 may provide the following benefits: (i) the inert gas may function as a fire suppressant within the LIBS system 10; (ii) the flow of the inert gas within the linkage assembly 16, due to the gas-tight configuration of the inert gas assembly 24, may help prevent dust and other contaminants from entering the laser cabinet and damaging the laser optics; and (iii) the inert gas may function as a signal enhancer for the laser data collection.

Generally, in various embodiments, the zero-leak valve 26 is closed while inert gas is pumped into the inert gas flange 54 and the lens housing 56. After filling the inert gas flange 54 and lens housing 56 with the inert gas, the zero-leak valve 26 may then be opened to then allow the inert gas to flow into the purge head 22 and the sample supply chamber 14.

As shown in FIGS. 10 and 11, the lens housing 56 may comprise a solid lens 62 and a separate lens 64 comprising an aperture 68. In certain embodiments, the aperture 68 may positioned in the center of the lens 64. The aperture 68 may have a diameter of at least 1, 2, 3, 4, 5, or 6 mm and/or less than 25, 20, 15, 10, 9, 8, or 6 mm. Generally, the aperture 68 needs to be large enough to facilitate the transfer of the inert gas, but small enough to mitigate the introduction of the particulate sample into the lens housing 56.

Additionally or alternatively, in various embodiments, the lens 64 with aperture 68 may comprise at least 1, 2, 3, 4, 5, 6, 7, 8, additional apertures, in addition to the center aperture 68, that surround the center aperture 68. In such embodiments, these additional apertures may have a smaller diameter than the center aperture 68 and, consequently, can help mitigate the flow back of the inert gas into the lens housing 56. In other words, these additional apertures (not pictured) may be useful in enhancing the thrust vectoring properties of inert gas assembly 24.

Generally, the lens 64 with aperture 68 is the lens that faces the purge head 22 and sample supply chamber 14, whereas the solid lens 62 will face the laser cabinet 12.

In various embodiments, the solid lens 62 does not contain any apertures and is a solid lens that is able to prevent the flow of any fluids or solids from leaving the lens housing 56. Consequently, this can prevent the introduction and contamination of the laser housing 12 from any particulate samples or other contaminants that may inadvertently get introduced into the linkage assembly 16.

Figure 9:
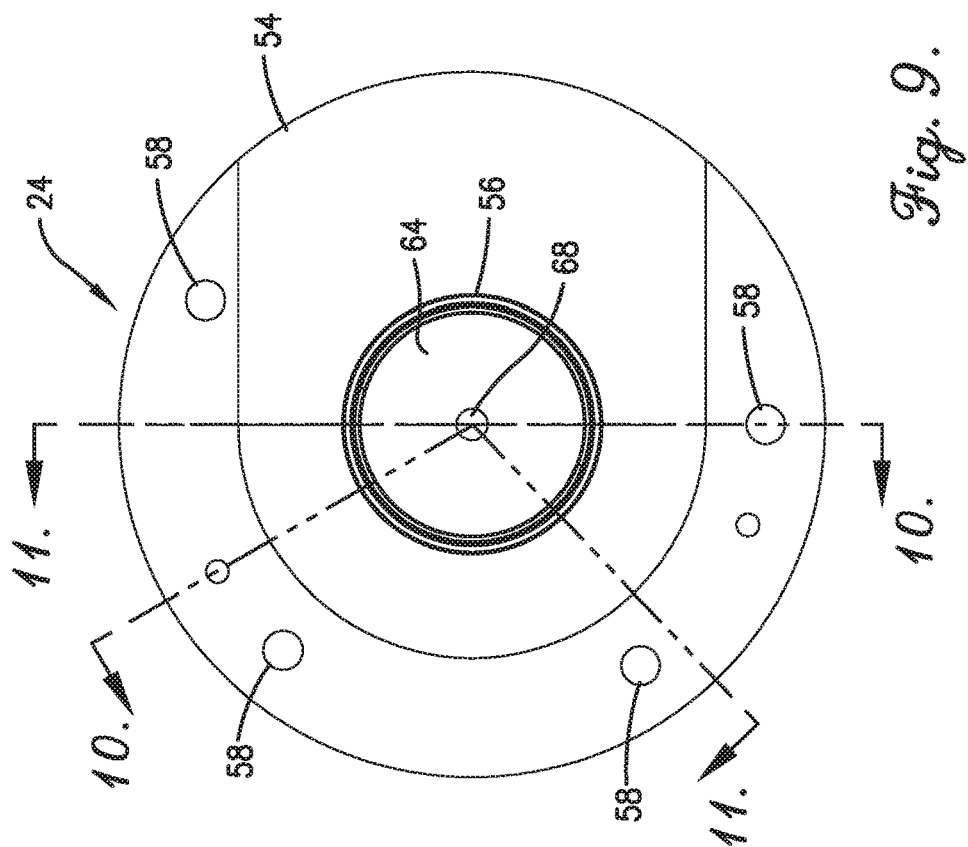
FIG. 9 depicts a front elevation view of the inert gas assembly of the linkage assembly according to one embodiment of the present invention.
Figure 8:
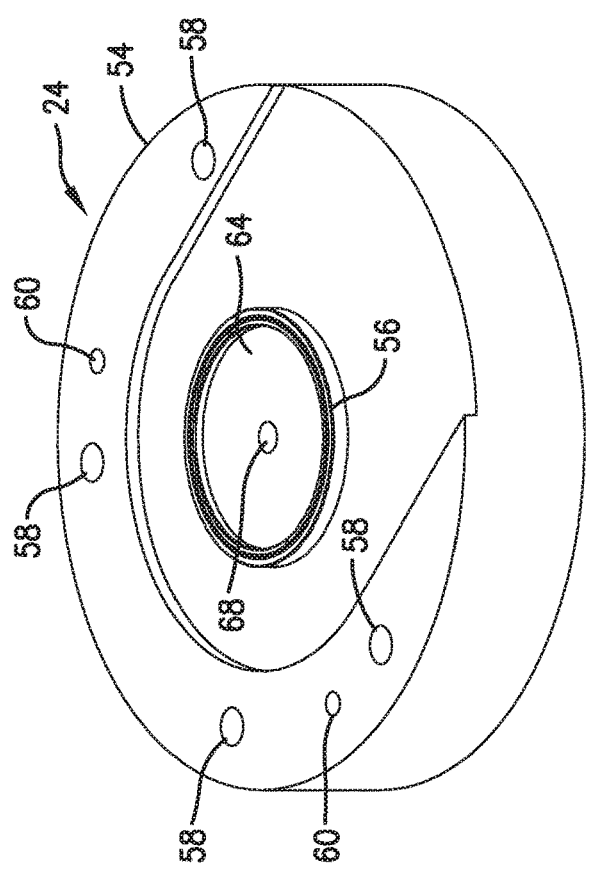
FIG. 8 depicts a front perspective of the inert gas assembly of the linkage assembly according to one embodiment of the present invention.

As shown in FIGS. 8 and 9, the lens 62 and 64 may have a circular shape. Moreover, the lens 62 and 64 may be produced with any transparent material capable of effectively transmitting lasers. In certain embodiments, the lens 62 and 64 may be made from glass, a polycarbonate, or a polyolefin.

The lens housing 56 may be held in place with one or more O-rings 70, as shown in FIGS. 10-12. Consequently, the lens housing 56 may be easily removed from the inert gas flange 54 due to the use of these O-rings. As shown in FIGS. 8 and 9, the O-rings may protrude out from the lens housing 56. The double O-ring arrangement 70 allows for the inert gas to be delivered to the center of the lens housing 56 through the inert gas intake 66.

Generally, the inert gas flange 56 may be designed and manufactured out of various metal alloys, preferably stainless steel. Moreover, in various embodiments, the inert gas flange 56 may be coated with a spray-on durability coating to help increase the durability of the purge head 22. Exemplary durability coatings may include ceramic-based coatings.

The method of using the LIBS system 10 is now described in greater detail below. During operation of the LIBS system 10, the particulate sample to be tested, such as coal, may be introduced into the sample supply chamber 14 and will subsequently contact the tapered front face 42 of the purge head 22. Subsequently, the particulate sample may be ablated with the laser upon contacting the tapered front face 42 of the purge head 22. Once ablation of the sample material occurs, light is emitted from the resulting plasma plume. That light may be captured by spectrometers located in the laser cabinet 12. The captured LIBS spectral data may then be sent from the spectrometers to a computer for further analysis. Based on this analysis, the feed rate of the feeding system 18 may be adjusted accordingly based on the characteristics and properties of the tested particulate sample.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

CLAIMS NOT LIMITED TO DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. A linkage assembly for a laser-induced breakdown spectroscopy system, said linkage assembly comprising a purge head, wherein said purge head comprises:
   (a) a base for connecting said purge head to said linkage assembly;
   (b) a protrusion protruding from said base for at least partially extending into a sample supply chamber, said protrusion comprising a tapered front face and a slot opening positioned between said base and said tapered front face; and
   (c) a perforation extending through said base and said protrusion, wherein said perforation is configured to allow a laser to pass through and contact a sample.

2. The linkage assembly according to claim 1, wherein said tapered front face comprises a shaped opening extending from said tapered front surface to said slot opening.

3. The linkage assembly according to claim 2, wherein said shaped opening comprises an angle of at least 5 degrees and less than 80 degrees.

4. The linkage assembly according to claim 2, wherein said tapered front surface has an angle of at least 25 degrees and less than 85 degrees relative to a longitudinal axis of said purge head.

5. The linkage assembly according to claim 2, wherein the length of said protrusion constitutes at least 25 percent of the overall length of said purge head.

6. The linkage assembly according to claim 2, wherein shaped opening comprises a maximum width, wherein said maximum width of said shaped opening is greater than average width of said perforation.

7. The linkage assembly according to claim 1, wherein said linkage assembly further comprises a leak-resistant valve and inert gas assembly comprising an inert gas flange and a lens housing.

8. A laser-induced breakdown spectroscopy system, said laser-induced breakdown spectroscopy system comprising:
   (a) a laser housing comprising a laser source and a spectrometer; and
   (b) a linkage assembly for connecting said laser housing to a sample supply chamber, wherein said linkage assembly comprises a purge head, said purge head comprising—

(i) a base for connecting said purge head to said linkage assembly;
(ii) a protrusion protruding from said base for at least partially extending into a sample supply chamber, said protrusion comprising a tapered front face and a slot opening positioned between said base and said front face; and
(iii) a perforation extending through said base and said protrusion, wherein said perforation is configured to allow a laser to pass through and contact a sample.

9. The laser-induced breakdown spectroscopy system according to claim 8, wherein said tapered front face comprises a shaped opening extending from said tapered front surface to said slot opening.

10. The laser-induced breakdown spectroscopy system according to claim 9, wherein said shaped opening comprises an angle of at least 5 degrees and less than 80 degrees.

11. The laser-induced breakdown spectroscopy system according to claim 9, wherein said tapered front surface has an angle of at least 25 degrees and less than 85 degrees relative to a longitudinal axis of said purge head.

12. The laser-induced breakdown spectroscopy system according to claim 9, wherein the length of said protrusion constitutes at least 25 percent of the overall length of said purge head.

13. The laser-induced breakdown spectroscopy system according to claim 9, wherein shaped opening comprises a maximum width, wherein said maximum width of said shaped opening is greater than average width of said perforation.

14. The laser-induced breakdown spectroscopy system according to claim 8, wherein said linkage assembly further comprises a valve and inert gas assembly comprising an inert gas flange and a lens housing.

15. A method for operating a laser-induced breakdown spectroscopy system, said method comprising:
(a) providing a laser housing comprising a laser source and a spectrometer connected to a sample supply chamber via a linkage assembly, wherein said linkage assembly comprises a purge head, said purge head comprising—
(i) a base for connecting said purge head to said linkage assembly;
(ii) a protrusion protruding from said base for at least partially extending into a sample supply chamber, said protrusion comprising a tapered front face and a slot opening positioned between said base and said front face; and
(iii) a perforation extending through said base and said protrusion, wherein said perforation is configured to allow a laser to pass through and contact a sample;
(b) contacting said sample with said laser when at least a portion of said sample contacts said tapered front face of said purge head.

16. The method according to claim 15, wherein said tapered front face comprises a shaped opening extending from said tapered front surface to said slot opening.

17. The method according to claim 16, wherein said shaped opening comprises an angle of at least 5 degrees and less than 80 degrees.

18. The method according to claim 16, wherein said tapered front surface has an angle of at least 25 degrees and less than 85 degrees relative to a longitudinal axis of said purge head.

19. The method according to claim 16, wherein the length of said protrusion constitutes at least 25 percent of the overall length of said purge head.

20. The method according to claim 16, wherein said linkage assembly further comprises a valve and inert gas assembly comprising an inert gas flange and a lens housing.

\* \* \* \* \*